US011045503B2

(12) United States Patent
Moreno Gonzalez

(10) Patent No.: US 11,045,503 B2
(45) Date of Patent: Jun. 29, 2021

(54) PHARMACEUTICAL COMPOSITION FOR PREVENTING, TREATING AND CURING ROSACEA, COMPRISING SNAIL SLIME, CHAMOMILE AND PROPOLIS

(71) Applicant: MUCIDERM S.A., Santiago (CL)

(72) Inventor: Elmo Moreno Gonzalez, Santiago (CL)

(73) Assignee: MUCIDERM S.A., Santiago (CL)

( * ) Notice: Subject to any disclaimer, the term of this patent is extended or adjusted under 35 U.S.C. 154(b) by 170 days.

(21) Appl. No.: 15/510,306

(22) PCT Filed: Oct. 17, 2014

(86) PCT No.: PCT/CL2014/000054
§ 371 (c)(1),
(2) Date: Mar. 10, 2017

(87) PCT Pub. No.: WO2016/054757
PCT Pub. Date: Apr. 14, 2016

(65) Prior Publication Data
US 2017/0281690 A1    Oct. 5, 2017

(30) Foreign Application Priority Data

Oct. 10, 2014   (CL) .................................. 2729-2014

(51) Int. Cl.
| | | |
|---|---|---|
| A61K 35/618 | (2015.01) |
| A61K 35/644 | (2015.01) |
| A61K 36/28 | (2006.01) |
| A61L 15/40 | (2006.01) |
| A61K 9/00 | (2006.01) |
| A61K 9/06 | (2006.01) |
| A61K 9/70 | (2006.01) |
| A61K 31/01 | (2006.01) |

(52) U.S. Cl.
CPC .......... *A61K 35/618* (2013.01); *A61K 9/0014* (2013.01); *A61K 9/06* (2013.01); *A61K 9/7023* (2013.01); *A61K 31/01* (2013.01); *A61K 35/644* (2013.01); *A61K 36/28* (2013.01); *A61L 15/40* (2013.01)

(58) Field of Classification Search
None
See application file for complete search history.

(56) References Cited

U.S. PATENT DOCUMENTS

2013/0309296 A1    11/2013    Moreno Gonzalez et al.
2015/0056175 A1    2/2015    Garcia Gilabert

FOREIGN PATENT DOCUMENTS

| ES | 2443816 A1 | 2/2014 |
| WO | 9215276 A2 | 9/1992 |
| WO | 0166079 A1 | 9/2001 |
| WO | 2009002982 A2 | 12/2008 |
| WO | 2014085876 A1 | 6/2014 |

OTHER PUBLICATIONS

Dimosthenis Tsoutsos, Despoina Kakagia & Konstantinos Tamparopoulos, The efficacy of Helix aspersa Müller extract in the healing of partial thickness burns: A novel treatment for open burn management protocols, Journal of Dermatological Treatment, 2009, pp. 219-222, vol. 20, No. 4.
A. Brieva, N. Philips, R. Tejedor, A. Guerrero, J.P. Pivel, J.L. Alonso-Lebrero, S. Gonzalez, Molecular Basis for the Regenerative Properties of a Secretion of the Mollusk Cryptomphalus aspersa, Skin Pharmacology and Physiology, 2008, pp. 15-22, vol. 21, No. 1.
The International Searching Authority, Notification of Transmittal of the International Search Report and the Written Opinion of the International Searching Authority or the Declaration, May 22, 2015.
Jarmuda, et al., Correlation between serum reactivity to Demodex-associated Bacillus oleronius proteins, and altered sebum levels and Demodex populations in erythematotelangiectatic rosacea patients, Journal of Medical Microbiology vol. 63, Issue 2, 2014, 258-262, last retrieved on Mar. 24, 2020, www.microbiologyresearch.org/content/journal/imm/10.1099/jmm.0.065136-0#html_fulltext.
Jarmuda, et al., Potential role of Demodex mites and bacteria in the induction of rosacea, Journal of Medical Microbiology vol. 61, Issue 11, 2012, 1504-1510, last retrieved on Mar. 24, 2020, www.microbiologyresearch.org/content/journal/jmm/10.1099/jmm.0.048090-0.

*Primary Examiner* — Michael Barker
(74) *Attorney, Agent, or Firm* — Gottlieb, Rackman & Reisman, P.C.

(57) ABSTRACT

The invention relates to a pharmaceutical composition consisting of snail slime *Helix aspersa* muller (*Cryptomphalus aspersus*) (20% to 50%), camomile extract (1-4%), propolis 1l-4%), and pharmaceutically acceptable excipients and/or additives for forming a formulation of low, intermediate or high viscosity (10 to 1000 Pa-s). Said composition is in the form of a lotion, soap, cream or gel, which is embedded in a gauze-type fabric in the form of a plaster that can be applied to lesions caused by the different types of rosacea. The composition can also contain natural extracts such as marigold extract, honey and vegetable oils. The invention also relates to the method for producing the composition and to the use thereof for preparing a medicament or device for preventing, treating or curing lesions caused by rosacea, on the skin of the face or the body.

8 Claims, 3 Drawing Sheets a)

b)

c)

PHARMACEUTICAL COMPOSITION FOR PREVENTING, TREATING AND CURING ROSACEA, COMPRISING SNAIL SLIME, CHAMOMILE AND PROPOLIS

The present application is a national phase filing of PCT/CL2014/000054, filed on Oct. 17, 2014 and now pending, which claims priority to Chile Patent Application No. 2729-2014, filed Oct. 10, 2014, also pending. Both applications are incorporated by reference.

DISCUSSION OF PRIOR ART

*Rosacea* is a rare, inflammatory and chronic skin disease characterized by redness in the central part of the face with periodic exacerbations and remissions. When rosacea progresses, other signs and symptoms, such as semi-permanent erythema, telangiectasia, papules, pustules, ocular redness, burning, burning and itching may develop. In some cases, thickening of the skin occurs, especially notorious and characteristic when it affects the nose (rhinophyma) (Schmutz, 2014; Tuzun et al, 2014).

Although it usually affects mainly women, rosacea tends to be more severe in men. Although it appears between 30 and 40 years old, the disease manifests aggressively between the 40 and 50 years old. Among the main symptoms of rosacea we can find erythema, persistent redness, dilated blood vessels, or the appearance of papules and pustules in the central area of the face. In addition, in the advanced stages of the disease, swelling may occur in the nose or other areas of the face due to hyperplasia of the (i) sebaceous glands.

It is estimated that *Rosacea* affects more than 45 million people worldwide. It affects people with white skin, generally people of European Northwest ancestry. In Britain and Ireland it is nicknamed "the curse of the Celts" (Schmutz, 2014, Tan & Berg, 2013).

Although the exact etiology of rosacea is not well known, it is now widely accepted that it is a chronic inflammatory condition that occurs in the context of an impaired immune response. The current model for the etiology of rosacea suggests that environmental changes induced by microbes (such as *Demodex folliculorum*), hormonal changes, or exposure to UV light can be detected by pattern recognition receptors of the immune system. Subsequent effector molecules induce certain signaling pathways, such as cytokines, chemokines and cathelicidin. Reactive oxygen species (ROS) can then modify the cutaneous structure through vascular changes, lymphocyte infiltration, neutrophil recruitment, and collagen degradation, which may perpetuate this response. According to this, most of the current therapies are intended to modulate various points of this inflammatory cascade (Schmutz, 2014; Cribier, 2014).

Classification

In April 2002, an expert committee was set up by the National *Rosacea* Society Expert Committee, which explicitly defined rosacea and proposed a clinical classification in 4 different subtypes, based on predominant symptoms and signs (Sanz-Motilva, 2012). Patients may have more than one of the following subtypes:

1.—Erythematous-telangiectatic rosacea: permanent reddish color (erythema) is observed, with a tendency to easily redden. It is also common to have small visible blood vessels near the surface of the skin (telangiectasia) and possibly burning and itching sensation.

2.—Papulo-pustular rosacea: there is some permanent reddish coloration with reddish pimples (papules) that may contain pus (pustules) (typically lasting from 1 to 4 days); This subtype can be easily mistaken for acne.

3.—*Rosacea*-Fimatosa: subtype very commonly associated with rhinophyma (a thickening of the nose). Symptoms include thickening of the skin, irregular surface nodules, and enlargement. It can also affect the chin (gnatophyma), forehead (metophyma), cheeks, eyelids (blepharophyma), and ears (otophyma). [2] Small visible superficial blood vessels (telangiectasias) can be seen.

4.—Ocular rosacea: in this subtype the eyes and eyelids are red, dry and irritated. Some other symptoms include foreign body sensation, itching and burning.

There are other descriptive terms applied to rosacea presentations, but these are not formally accepted as subtypes of rosacea, such as granulomatous rosacea, and the rare and severely damaging *Rosacea fulminans* (*pyoderma faciale*) occurring exclusively in women after adolescence and more commonly after turning 20 years.

Clinical Picture

This ailment can be confused and in some cases co-exist with *acne vulgaris* and/or seborrheic dermatitis. The presence of redness in the scalp or ears suggests a different diagnosis or co-existence, since rosacea is mainly a facial diagnosis (Cribier, 2014; Sarnoff, 2014).

Patients suffering from rosacea often report periods of depression, psychological damage or loss of self-esteem due to disfigurement and burning sensations, and a subsequent decrease in quality of life. These resulting ailments can cause patients to become increasingly isolated, restricting their predisposition to minimal social interaction and even think about suicide (Huynh, 2013).

Treatment options for rosacea (Del Rosso et al., 2014, Sarnoff, 2014, Chang et al., 2014, Moustafa et al., 2014)

*Rosacea* is a chronic skin disease, but it is possible to control with medical treatment and some changes in lifestyle. Depending on the severity of the clinical symptoms, dermatologists recommend a personalized treatment. Another important element to control rosacea is to identify and avoid the triggers (factors that cause erythema or outbreaks of skin lesions). Some of these best-known factors are exposure to UV radiation, extreme weather conditions, alcohol consumption, spicy food or hot drinks. To minimize the harmful impact of rosacea-inducing factors, a constant protection against UV radiation (e.g., by the use of sun protection products with highly effective anti-UV filters) is recommended, stay in fresh rooms when outside is hot, wear protective clothing such as wide-brimmed hats or scarves in case of exposure to extreme weather, reduce consumption of hot drinks and spicy foods. Since the skin is very sensitive to irritations, only soft skin care products should be used. Establishing a proper daily regimen for skin care can help to control redness.

*Rosacea* is a disease that can last quite a bit, improve slightly and then get worse if it is not treated with time and properly, the goal is to control its symptoms and make the skin look its best. This disease has no cure, but in some cases can be controlled.

For the treatment of rosacea there are several alternatives that allow controlling the outflow of grains and bulges caused by the disease. The most difficult to treat is erythema of the skin, since the most common medicines are the antibiotics that can take up to two months to exert their effect. More radically, other means such as laser surgery or using a thin electric needle can be used for those grains that arise on the face.

The following are the main treatments for pathology:

Systemic Therapy

Although a bacterial pathogen has not been clearly implicated in the pathophysiology of rosacea, antibiotics have numerous anti-inflammatory properties, including suppression of neutrophil migration and its chemotaxis, inhibition of angiogenesis, Production of matrix metalloproteinases (MMPs) and inhibition of lymphocyte activation, proliferation and migration, and activation of anti-inflammatory cytokines. In this regard, the most common systemic drugs include doxycycline, erythromycin, minocycine, tetracycline, metronidazole, and occasionally low doses of isotretinoin. Low-dose sub-antimicrobial oral doxycycline have been shown to be effective with less risk of affecting endogenous flora and less likely to develop resistant strains.

Topical Therapeutic Options

The most common topical medications include azelaic acid, metronidazole, erythromycin, and sodium or sulfur sulfacetamide 10% 5%. Recently, 1% cream pimecrolimus has been found to be effective for mild to moderate rosacea.

The choice of vehicle (lotion, cream, foam gel) may influence tolerability in patients who often have a high sensitivity of the skin. Many patients with rosacea with very sensitive skin try herbal remedies and botanicals, such as feverfew, turmeric, colloidal oatmeal, niacinamide and quassia extract. In addition, other alternative therapies, such as colloidal silver, emulsified oil, oregano oil and vitamin K have been promoted as possible ways to treat rosacea. While many of the ingredients are promising, there is a lack of data on the effects of these cosmetics and more studies are required.

Lasers and Light Sources

Both the pulsed dye laser and intense pulsed light are treatments that have been found to be effective in reducing erythema of rosacea by selectively targeting the red pigment of hemoglobin in blood vessels, thermally blood clotting, and destruction of blood vessels walls without damaging the skin.

Lifestyle Modifications

By modifying some lifestyles you can significantly reduce the incidence of rosacea, avoiding triggers (heat, cold, wind, sun exposure, emotional problems), changes in diet (spicy food, alcohol), the use of sunscreen daily, gentle cleansers and skin care are very useful measures to control rosacea. Cosmetics to conceal or disguise can counteract redness and are therefore useful adjuncts to improve quality of life and self-esteem in managing this chronic condition.

Latest Market Trends for the Treatment of *Rosacea*

Alpha-adrenergic agonists such as brimonidine tartrate and oxymetazoline have potent vasoconstricting abilities and anti-reddening effects, making them very useful in the treatment of rosacea. They are currently in eye drops for glaucoma and a nasal decongestant spray, respectively. The 0.33% topical brimonidine tartrate was approved by the FDA in September 2013 for the treatment of persistent facial erythema of rosacea. On the other hand, a topical form of oxymetazoline has also been shown to be a potent partial agonist of alpha-1 and alpha-2 receptors, reducing facial erythema. However, there are no good controlled and randomized clinical trials for these drugs.

In addition, oral and topical ivermectin has been studied for the treatment of papulo-pustular rosacea, showing benefits; however, only topical ivermectin 1% cream has been studied in randomized controlled clinical trials.

In conclusion, as our understanding of the etiology of rosacea continues to evolve, so will our options for therapeutic interventions. Accordingly, the author of the present invention has investigated the potential of various formulations based on natural and snail slime products of the *Helix aspersa* Müller snail as a therapeutic and cosmetic alternative for this pathology.

*Helix aspersa* Müller

The common garden snail *Helix aspersa* Müller, also known as *Cryptomphalus aspersus* is a gastropod mollusk of terrestrial life that belongs to the order Pulmonata. It is one of several species of the genus *Helix*, very similar, and also denominated snails. Other names used are *Cryptomphalus aspersus, Cornu aspersum* and *Cantareus aspersus*. To move itself it requires the secretion of a mucus or drool, which when solidified serves as a support that isolates it from the unfavorable environment (operculation). It is hermaphrodite, oviparous and has a calcareous shell coiled in a spiral. Snail drool suitable for cosmetic application is obtained from fasting snails, which have been subjected to a state of stress by safe stimulation (by radiation or mechanical stress). This stimulation does not alter the survival of the animal and can be repeated several times during its life cycle. The slime secreted before these external stimuli has capacity to repair the skin of the snail and to protect it of the external aggressions. These properties can be extrapolated for the formulation and application of cosmetic preparations (Abad R, 1996).

Snail drool, particularly of the species *Cryptomphalus aspersus* or *Helix aspersa* Müller, is constituted mainly by the following active principles, considered the most relevant:

Allantoin (glyoxyl-diurea): a stimulant of cellular proliferation of the skin. It helps to eliminate necrotic, non-viable tissues, replacing them with new tissues and is anti-irritant. It promotes and accelerates the natural healing processes in the body. It has also been mentioned as a cell proliferator and epithelial stimulant and helps to clean and eliminate necrotic tissue, accelerating the growth of healthy new tissue (Sznitowska M & Janicki S, 1988). The FDA has not recognized allantoin as a wound-healing agent, but as a skin protector, classified within category I (safe and effective).

Glycolic acid (hydroxyacetic acid): It is a natural organic compound of small molecular chain, which allows it to penetrate the skin more quickly to deeper layers. This acid is widely used in dermatological treatments, mainly to fade in any section of skin wrinkles, stretch marks, scars, to decrease acne. As an irritant, it is recommended to use it with plant extracts, collagen and vitamins that support cell reconstruction (Denda S, 2010). The action of this treatment is to decrease the thickness of the stratum corneum of the skin and to increase the thickness of the stratum of Malpigio. It is also an excellent exfoliator and helps other components to penetrate the skin more easily (Elson M L, 1993, Tribó et al, 2004).

Elastin: 70 kDa protein, present in all vertebrates, with structural functions that provides resistance and elasticity to the tissues. It has a great capacity of expansion, which allows, in a treatment of wounds, the healing by expansion of the regenerating tissues (Sage & Gray, 1977; Young G L & Jewell D, 2000).

Collagen: This molecule allows the replacement of denatured collagen and the production of metalloproteinase inhibitors (TIMP), which facilitates regulation between the synthesis and degradation of the components of the dermis. It improves the cellular cytoskeleton, since it induces the proliferation and activation of the fibroblasts thanks to the beta-EGF activity. As a result, the production of hyaluronic acid, collagen and elastin fibers and the deposition of fibronectin in the extracellular matrix increases, thus favoring dermal support (Young G L & Jewell D, 2000).

Finally, the natural antibiotics contained in snail slime are substances capable of acting against bacteria normally present in the skin, especially *Eschericia Coli, Staphylococcus aureus, Pseudomona Aeruginosa* and *Acne vulgaris*, protecting against infection. Together with these more relevant components, the presence of vitamins and antibiotics is estimated to allow a greater rate of skin regeneration, a decrease in inflammation, and an inhibition of the infective processes characteristic of skin lesions, all of which are relevant aspects for the treatment of pathology such as rosacea.

In this regard, it is particularly noteworthy that the empirical evidence suggests that all the components of the snail slug, in particular, the Chilean species (*Helix aspersa müller*) act synergistically, a relevant aspect to be analyzed within the present application.

DETAILED DESCRIPTION OF THE INVENTION

The applicant of the present invention for some years has been devoted to the development of products based on snail drool obtained from domestic species. Its development has been eminently related to cosmetics, generating several products that include: hand, body and facial cream, shampoo, conditioning balm, bath soaps, all of them currently registered and marketed.

Considering that the components of snail slime have healing, regenerative, immunosuppressive and antiseptic properties, among others, it was considered to produce a mixed product, with components of natural origin, specifically formulated for the healing of the skin of patients with various types of rosacea.

The inventors of the present application initially evaluated the product in a dermo-cosmetic manner and as part of the popular use that is being given to the snail drool, clearly taking advantage of its extraordinary qualities that have been seen in some people with different skin conditions, particularly rosacea (FIG. 2). The product has been used as a complement for the treatments and it has been observed that the formulation with snail slime under study not only works as palliative but also curative for rosacea. Therefore, it is surprisingly clear that snail drool has an activity that exceeds conventional treatments, particularly on erythema and teleangiectasia produced in the disease.

The present invention is further directed to the development of an application/device, from the developed product, which will be more efficient and effective than the current treatment, which is essentially palliative. This treatment may, at best, stop the development of rosacea and completely eliminate erythema and teleangiectasia produced by the pathology. The use of the product may also allow the desquamation of dead skin and regeneration of new skin due to the properties already described of its components.

The product/composition is an application/device in the form of a patch or band (FIG. 3), easy to use for both qualified personnel and the patient himself, of variable size. Its use is complementary to any other treatment.

Previous research of the state of the art performed shows a series of scientific manuscripts describing the aforementioned traditional method and patents associated with the same compositions and procedures. By way of example, U.S. Patent Publication No. 2014/0161747 (compositions comprising avermectin/azelaic acid useful for treating e.g. rosacea) discloses a dermatological pharmaceutical type composition for the treatment of skin disorders, such as rosacea. These compounds have already been described in our memory and are not related to the present invention. In addition, the patent CN 103566208 refers to a formulation containing *scutellaria baicalensis, gardenia jasminoides*, peach kernel, *Chinese angelica, Szechuan lovage rhizome*, safflower, *Folium eriobotryae, Radix scrophulariae*, testicle and *Rhizoma phragmitis*, a combination of Chinese natural products that do not interfere in any way with the present invention.

Accordingly, it has been concluded that there is neither a national alternative nor a similar alternative to the formulation of the present invention nor its use for treating rosacea, so that this product would be novel, inventive and certainly with clear industrial application, The three fundamental aspects for the acceptance of a patent. Both the formulation and the form of application are not obvious because in previous analyzes of our group it has been possible to observe a synergy of its components in the treatment.

EXAMPLES

The examples set forth below are incorporated by way of illustration only in order to promote understanding of the specification and do not imply that they limit in any way the scope of the claims being sought.

Example 1: Formulation Example

A) Formulation of the Lotion

| Components | % |
|---|---|
| Water | 60.00 |
| Snail slime filtrate | 5.00 |
| Liquid Paraffin | 6.00 |
| Glycerin | 7.00 |
| Cetearyl alcohol (CETEARETH-20) | 3.00 |
| Polyisobutene hydrogenated | 3.00 |
| Dimethicone | 1.00 |
| Chamomille extract | 8.00 |
| PEG-100 glyceryl stearate/stearate | 1.00 |
| Propylene Glycol | 0.56 |
| Propolis | 3.50 |
| Tocopheryl acetate | 0.50 |
| Triethanolamine | 0.30 |
| Diazolidinyl Urea | 0.30 |
| Methyl Paraben | 0.26 |
| Acrylates/C10-30 alkyl acrylate cross-polymer | 0.20 |
| Perfume | 0.20 |
| Hydantoin DMDM | 0.14 |
| Propylparaben | 0.03 |
| Iodopropynyl Butylcarbamate | 0.01 |

B) Formulation of Soap

| Components | % |
|---|---|
| Water | 53.38 |
| Sodium lauryl sulfate | 10.00 |
| Snail slime filtrate | 20.00 |
| Chamomille Extract | 5.00 |
| Cocoamido propyl betaine | 3.00 |
| Propolis | 3.00 |
| Glycerin | 2.00 |
| Cocoamide DEA | 1.50 |
| Hydantoin DMDM | 0.60 |
| Sodium Chloride | 0.50 |
| Methylparaben | 0.20 |
| Propylparaben | 0.15 |

-continued

| Components | % |
| --- | --- |
| PEG-150 Stearate | 0.10 |
| Perfume | 0.50 |
| Citric acid | 0.07 |

C) Formulation for Body and Facial Cream

| Component | % |
| --- | --- |
| Water | 50.50 |
| Snail secretion filtrate | 20.00 |
| Liquid Paraffin | 6.00 |
| Chamomille Extract | 5.00 |
| Propolis | 3.00 |
| Glycerin | 5.00 |
| Cetearyl alcohol (CETEARETH-20) | 3.00 |
| Polyisobutene hydrogenated | 3.00 |
| Dimethicone | 1.00 |
| PEG-100 glyceryl stearate/stearate | 1.00 |
| Propylene Glycol | 0.56 |
| Tocopheryl Acetate | 0.50 |
| Diazolidinyl Urea | 0.30 |
| Methyl paraben | 0.26 |
| Acrylates/C10-30 alkyl acrylate cross-polymer | 0.20 |
| Perfume | 0.20 |
| Hidantine DMDM | 0.14 |
| Propylparaben | 0.03 |
| Iodopropynyl Butyl carbamate | 0.01 |
| Triethanolamine | 0.30 |

D) Formulation for Face and Body Gel
1. 50 g face and body cream (c)
2. 30 g of sterile snail slime,
3. 10 g of petroleum jelly
4. 10 mL of bi-distilled water or physiological saline Example 2: Manufacture of the Gel Patch Formulation For the manufacture of 15 to 20 gel patches the following procedure is performed:
50 grams of body cream are sterilized by autoclaving at 150° C., with a rise time of temperature, exposure time and cooling time (30 minutes), then 30 grams of sterilized *Hélix aspersa* Muller snail slime are added, homogenizes with stirring, then 10 ml liquid petroleum jelly and 10 ml bi-distilled water are added to maintain moisture. It is homogenized and then the patches are soaked with the gelatinous formulation having a viscosity of between 500 and 1,000 pa·s.

Example 3: Administration and Dosage

The product is applied as a lotion, cream, gel or patch containing these formulations, directly on the lesion as follows, in the following cases:
*Rosacea* Lesions on Face and Body Skin
The product is applied to the face and body of people with rosacea, as follows:
Case 1: *Rosacea erythematous-telangiectic* (FIG. 2a): the soap or gel is applied for one minute through the affected area. The treatment should be continued for at least 3 times a day and then rinsed with plenty of water to finally apply the body lotion/cream to the affected area. It is recommended to do this process twice a day.
Case 2: Papulo-pustular rosacea (FIG. 2b): In patients with severe rosacea lesions, with evident erythema, acne and severely irritating lesions, the gel patch (FIG. 3) should be applied to the affected area at night And leave it until the next morning, then wash the area with plenty of water and apply the body cream/lotion in the affected area. This process should be performed for 7 to 10 days.
Case 3. Fimatose rosacea (FIG. 2c): Apply the soap to the nose with a sponge, at least 5 times and then rinse with plenty of water. Then apply the body cream/lotion, until total absorption. It is recommended to do this process twice a day.

REFERENCES

Figure 1:
FIG. 1: Photograph of *Helix aspersa* Müller snail strain
Figure 2:
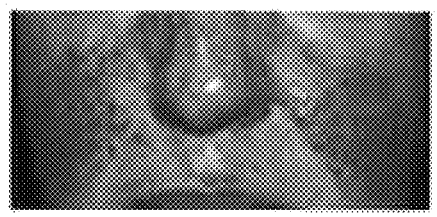
FIG. 2: Example of characteristic lesions of rosacea. a) Erythematous-telangiectic rosacea, b) Papulo-pustular rosacea, c) *Rosacea*-Fimatosa.
Figure 2:
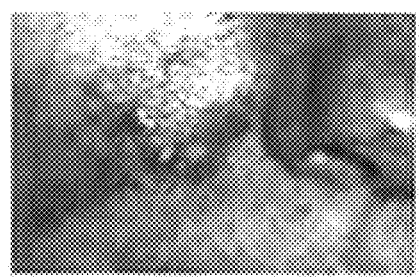
Figure 2:
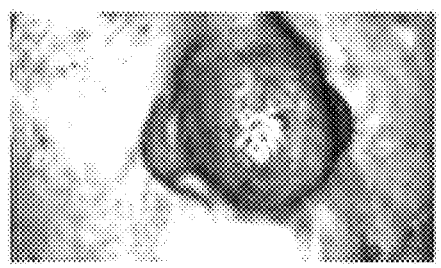
Figure 3:
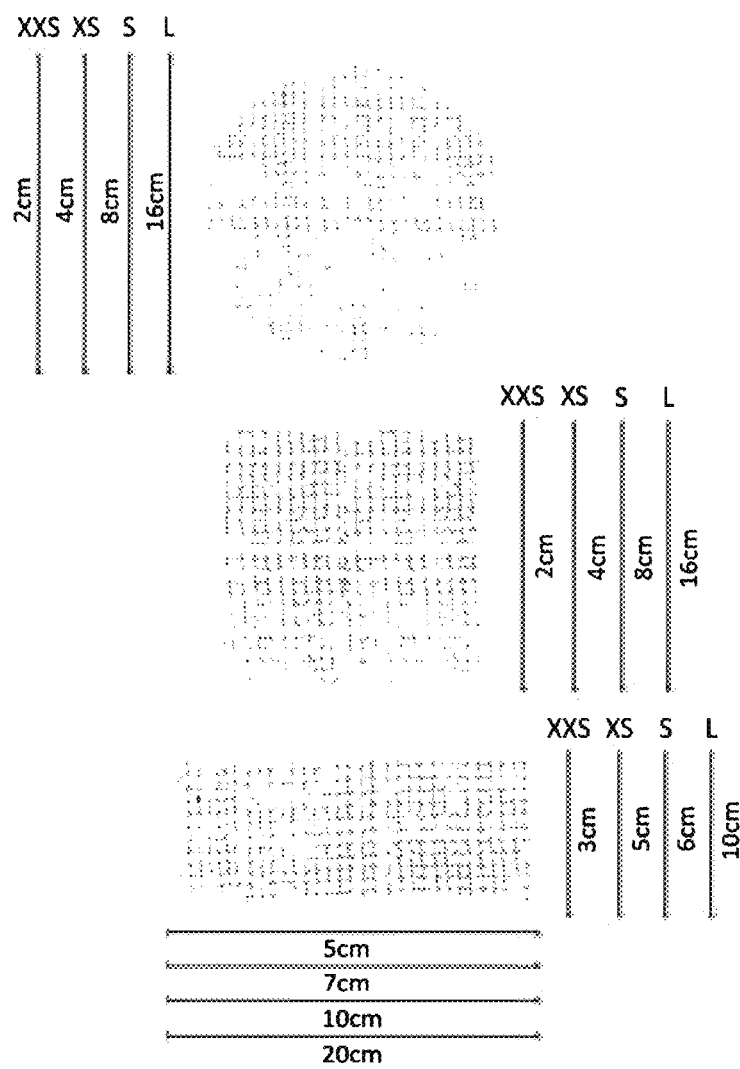
FIG. 3: Shape and dimensions of the various gauze patches or gel-embedded bandages of the invention for therapeutic purposes.

Abad R, Therapeutic and cosmetic compositions for treatment of skin, U.S. Pat. No. 5,538,740, 1996.
Chang B P, Kurian A, Barankin B. *Rosacea*: an update on medical therapies. Skin Therapy Lett. 2014 June; 19(3): 1-4.).
Cribier B. Physiopathology of rosácea. Ann Dermatol Venereol. 2014 September; 141 Suppl 2:S158-64.
Del Rosso J Q, Thiboutot D, Gallo R, Webster G, Tanghetti E, Eichenfield L F, Stein-Gold L, Berson D, Zaenglein. A Consensus recommendations from the American Acne &; *Rosacea* Society on the management of rosacea, part 5: a guide on the management of rosacea. Cutis. 2014 March; 93(3):134-8.
Denda S, Denda M, Inoue K, Hibino T. Glycolic acid induces keratinocyte proliferation in a skin equivalent model via TRPV1 activation. J DermatolSci. 2010 February; 57(2):108-13.
Elson M L. The molecular structure of glycolic acid and its importance in dermatology. Cosmetic Dermatology; 6(7): 35-40, 1993.
Huynh T T. Burden of Disease: The Psychosocial Impact of *Rosacea* on a Patient's Quality of Life. Am Health Drug Benefits 2013, 6(6): 348-354.
Moustafa F A, Sandoval L F, Feldman S R. *Rosacea*: new and emerging treatments. Drugs. 2014 September; 74(13):1457-65.
Sage E H & Gray W R 1977 Evolution of elastin and elastin structure, p 291. in; Advances in Experimental Medicine and Biology, vol. 79 L B Sandberg & C Franzblaw, eds) Plenum Press, NY & London).
Sarnoff D S. Therapeutic update on *Rosacea*. J Drugs Dermatol. 2014 January; 13(1):10-1. Review.
Schmutz J L. Signs and symptoms of rosácea. Ann Dermatol Venereol. 2014 September; 141 Suppl 2:S151-7.
Sznitowska M, Janicki S., The effect of vehicle on allantoin penetration into human skin from an ointment for improving scar elasticity. Pharmazie. 1988 March; 43(3): 218.
Tan J, Berg M. *Rosacea*: current state of epidemiology. J Am Acad Dermatol. 2013 December; 69(6 Suppl 1):S27-35.
Tribó M J, Parrado C, Rais B et al. Preliminary results of the efficacy of intensive treatment with *Cryptomphalus aspersa* (SCA) secretion in cutaneous photo-aging therapy. Med Cutanlber Lat Am. 2004; 32:265-270.

Tüzün Y, Wolf R, Kutlubay Z, Karakuş O, Engin B. *Rosacea* and rhinophyma. Clin Dermatol. 2014 January-February; 32(1):35-46.

Young G L, Jewell D. (2002). Creams for preventing stretch marks in pregnancy. Cochrane Database Syst Rev., (2): CD000066.

The invention claimed is:

1. A patch administrable to adhere to a patient comprising a pharmaceutical composition for treating erythematotelangiectatic rosacea lesions comprising active ingredients consisting of:
   up to 5% snail slime from Helix asperse Muller (*Cryptophalus aspersa*);
   from 5% up to 8% chamomile extract; and
   1-4% propolis;
   wherein said snail slime, chamomile extract and propolis are dissolved into a solution including one or more excipients, and said composition having a viscosity between 10-1000 Pa-s.

2. The patch of claim 1, wherein said viscosity is limited to 500 Pa S.

3. The patch of claim 1, wherein said composition is in the form of a lotion.

4. The patch of claim 1, wherein said composition is in the form of a soap.

5. The patch of claim 1, wherein said composition is in the form of a cream.

6. The patch of claim 1, wherein said composition further comprising at least one of nettle extract and calendula extract.

7. The patch of claim 5, wherein the ratio of cream to snail slime is about 5:3 and the composition viscosity is limited to between 500 and 1000 pa s.

8. The patch of claim 1, wherein said composition is in the form of a gel.

* * * * *